(12) United States Patent
Pfaff et al.

(10) Patent No.: US 9,222,931 B2
(45) Date of Patent: Dec. 29, 2015

(54) PLASMA OR SERUM SEPARATOR

(76) Inventors: Tim Pfaff, Augsburg (DE); Christina Pfaff, Regensburg (DE); Dominic Pfaff, Neuburg/Donau (DE)

( * ) Notice: Subject to any disclaimer, the term of this patent is extended or adjusted under 35 U.S.C. 154(b) by 27 days.

(21) Appl. No.: 14/126,117

(22) PCT Filed: Jun. 15, 2011

(86) PCT No.: PCT/EP2011/059942
§ 371 (c)(1),
(2), (4) Date: Dec. 13, 2013

(87) PCT Pub. No.: WO2012/171560
PCT Pub. Date: Dec. 20, 2012

(65) Prior Publication Data
US 2014/0134598 A1     May 15, 2014

(51) Int. Cl.
*A01N 1/02*     (2006.01)
*G01N 33/49*    (2006.01)
*G01N 33/72*    (2006.01)
*B01D 39/14*    (2006.01)

(52) U.S. Cl.
CPC ............ *G01N 33/491* (2013.01); *G01N 33/728* (2013.01)

(58) Field of Classification Search
None
See application file for complete search history.

(56) References Cited

U.S. PATENT DOCUMENTS

| 5,135,719 A | 8/1992 | Hillman et al. | |
| 6,220,453 B1 | 4/2001 | Kitajima et al. | |
| 2004/0129678 A1* | 7/2004 | Crowley et al. | 216/84 |
| 2014/0001058 A1* | 1/2014 | Ghaffari et al. | 205/792 |

FOREIGN PATENT DOCUMENTS

| EP | 0172462 A2 | 2/1986 |
| EP | 0392377 A2 | 10/1990 |
| EP | 1477804 A1 | 11/2004 |
| JP | 2002350428 A | 12/2002 |
| WO | 2006017703 A1 | 2/2006 |

OTHER PUBLICATIONS

International Search Report and Written Opinion for PCT/EP2011/059942, dated Mar. 2, 2012.
Reply filed in European Patent Office for EP Patent Application No. 11730247.1, dated Sep. 7, 2014.

* cited by examiner

*Primary Examiner* — Renee Claytor
*Assistant Examiner* — Michelle F Paguio Frising
(74) *Attorney, Agent, or Firm* — Bachman & LaPointe, P.C.

(57) ABSTRACT

A plasma or serum separator (10) for isolating plasma or serum from whole blood, comprises: a blood separation member (12), configured for separating blood applied to a first portion such that the plasma or serum of the blood is located in a second portion; a holding member (14) covering and holding the blood separation member (12); a blood introducing portion (16) formed in a portion of the holding member (14) covering the first portion; a plasma or serum sampling aperture (18) formed in a portion of the holding member (14) covering the second portion; and at least one plasma or serum collecting cavity (22) arranged at the second portion in fluid communication with the plasma or serum sampling aperture (18) for collecting plasma or serum leaving the blood separation member (12) through the plasma or serum sampling aperture (18).

15 Claims, 8 Drawing Sheets

PLASMA OR SERUM SEPARATOR

CROSS-REFERENCE TO RELATED APPLICATION

This is the 35 USC 371 National Phase of International Application No. PCT/EP2011/059942, filed Jun. 15, 2011, and published as WO2012/171560A1.

The present invention relates to a plasma or serum separator for isolating plasma or serum from whole blood and to a plasma or serum sampling method using the separator; particularly, to a plasma or serum separator and a plasma or serum sampling method, in a blood test, for rapidly isolating and sampling high purity plasma or serum in a liquid state or in a dry state even from a small amount of blood without using a centrifuge.

In a clinical chemistry test and a clinical immunologic test, many of rapid tests for qualitative and quantitative diagnosis have been developed in the field of a hospital-related examination using blood as a sample.

Though part of the clinical tests can be carried out on whole blood, it is necessary to use plasma or serum isolated from a blood sample in order to attain a correct result of the test. If not isolated, red blood cells or an impurity in a blood sample blocks reflected light, transmitted light and emission measured in the test, affecting the measurement adversely.

Measurement on the kind and concentration of a blood component in a clinical laboratory test is usually performed such that whole blood is sampled with a blood collecting device, the sampled whole blood in a blood sampling tube is centrifuged to obtain serum or plasma and the obtained serum or plasma is used as a test sample.

Centrifugation, however, requires hundreds of μL or more of the whole blood amount and further consumes labor and time. Especially, in many fields of biochemical examinations, the presence of blood cells such as red blood cells disturbs the examinations; therefore, the serum or plasma is isolated from the blood in advance and used as a test sample. Hence, a necessity arises for a process in which blood sampled from a patient or a subject is at first coagulated in advance of an examination and then centrifuged to thereby obtain serum. While in Clinical Chemistry Analyzers available in recent years, a necessary mount of a test sample used in any of most examinations is as small as in the range of from several μL to tens of μL because of advancement in technology, a sampled blood amount depends on specifications of a centrifuge and a size of a blood sampling tube, which wastefully requires a blood amount more than necessary.

In the conventional centrifugal separation method, with a smaller test sample amount, separated red blood cells are re-suspended in plasma or serum; a problem arises that it is difficult to obtain only plasma or serum. Therefore, in the centrifugal separation method, a test sample amount has to be in the range of from hundreds of μL to several mL, which necessitates a syringe to sample blood, having led to a fault that a great burden is imposed on a person to be examined. Furthermore, since the centrifugal separation method requires a special apparatus for centrifuging and is carried out only in batches, it is disadvantageous in cost for treatments on small number of test samples and unsuitable for an on-demand and instant treatment.

A method of measuring a bilirubin concentration of a neonate is such that a blood-sampling needle is stuck in a sole of the neonate to sample blood with a capillary tube. Sampled blood is separated to obtain serum or plasma by a centrifuge for capillaries and a bilirubin concentration is attained by conversion of an absorbance in the proximity of a wavelength in the range of from 450 to 460 nm, which is a bilirubin absorption wave length, measured with a photometer dedicated thereto as shown in FIG. 1. Therefore, in order to perform the examination, a centrifuge for exclusive use has been required and a time has been consumed in separating operation longer than in measurement itself.

In FIG. 1, reference numeral 50 designates a light source; 52, a optical light chopper; 54, a heat absorbing filter; 56, a lens; 58, a filter disk; 60a and 60b, interference filters; 62, a capillary tube; 64, a capillary tube holder; 66, a photodiode; 68, an amplifier; and 70, a meter. The capillary tube 62 in which plasma or serum isolated from blood is accommodated is to be held on the capillary tube holder 64 and light from the light source 50 is to be passed through the optical light chopper 52, the heat absorbing filter 54, the lens 56 and the interference filters 60a and 60b and is irradiated to the capillary tube 62, thereby an absorbance being measured at a wavelength in the proximity of a value in the range of from 450 to 460 nm with the photodiode 66 to detect a bilirubin concentration with the meter 70.

As a means to solve the above problem, there has been known dry chemistry. This test is conducted such that a small amount of blood is dropped onto a plate constructed with a plasma or serum separation layer, which is a fiber filter such as a filter made of glass fibers; and a reaction layer located in the lower layer, and then plasma or serum is isolated in the plasma or serum separation layer and a reaction and a color development occur in the lower layer, which is subjected to colorimetry. The dry chemistry is a simple and convenient method not requiring troublesome sampling of plasma or serum with a centrifuge, whereas the test can be applied only to a system for exclusive use, in which the plasma or serum separation layer and the reaction layer is integrated into one piece. Since one plate can be used to measure only one examination item, plural plates are required for examining plural items; therefore, the dry chemistry is too expensive for its simplicity and convenience to be used widely.

EP 1 477 804 A1 provides a plasma or serum separator and a plasma or serum sampling method capable of isolating plasma or serum with good efficiency from a small amount of blood without using a centrifuge and without causing leakage of a blood cell component or hemolysis, and in addition, capable of isolating and collecting plasma or serum from a whole blood test sample in a short time with simplicity in a blood test in the scene of medical care requiring an instant treatment any time such as an emergency test, home-use test or the like. The plasma or serum separator for isolating plasma or serum from whole blood comprises: a blood separation member, a holding member covering and holding the blood separation member; a blood introducing portion formed in a portion of the holding member covering a proximal end portion of the blood separation member; and a plasma or serum sampling aperture formed in a portion of the holding member covering a distal end portion of the blood separation member, wherein the whole blood is introduced into the blood separation member through the blood introducing portion, the introduced whole blood is separated such that the plasma or serum is located in the distal end portion of the blood separation member, while blood cells are located in the proximal end portion of the blood separation member; thereby enabling the plasma or serum located in the distal end portion of the blood separation member to be sampled through the plasma or serum sampling aperture.

However, the plasma or serum located in the distal end portion of the blood separation member still needs to be transferred from the blood separation member to the analysis device, e.g. to the capillary tube of a photometer as shown in FIG. 1.

This transfer is laborious and includes the risk that some of the plasma or serum is lost or spoiled during the transfer.

It is therefore an object of the invention to provide an improved plasma or serum separator and an improved plasma or serum separator sampling method which are easy to handle and reduce the risk of plasma or serum being lost or spoiled.

The invention provides a plasma or serum separator according to independent claims 1 and a method for sampling blood or serum according to claim 11. The dependent claims define preferred embodiments of the apparatus or the method according to the independent claims, respectively. The invention further comprises methods for analyzing blood plasma or serum according to claims 14 and 15.

A plasma or serum separator for isolating plasma or serum from whole blood, comprises:
- a blood separation member, configured for separating blood applied to a first portion of the blood separation member such that the plasma or serum of the blood is located in a second portion of the blood separation member, while blood cells are located in the first portion of the blood separation member;
- a holding member covering and holding the blood separation member;
- a blood introducing portion formed in a portion of the holding member covering a first portion of the blood separation member;
- a plasma or serum sampling aperture formed in a portion of the holding member which covers the second portion of the blood separation member, and
- at least one plasma or serum collecting cavity arranged at the second portion of the blood separation member in fluid communication with the plasma or serum sampling aperture for collecting plasma or serum leaving the blood separation member through the plasma or serum sampling aperture.

A plasma or serum sampling method employing a plasma or serum separator according to the invention, comprises the steps of:
- applying blood to the blood introducing portion of the plasma or serum separator introducing whole blood into the blood separation member;
- subjecting the introduced whole blood to separation by the blood separation member such that the plasma or serum is located in the second portion of the blood separation member, while blood cells are located in the first portion of the blood separation member;
- transferring plasma or serum staying in the second portion of the blood separation member through the plasma or serum sampling aperture into the plasma or serum collecting cavity.

By transferring the plasma or serum into the collecting cavity the plasma or serum is provided by the plasma or serum separator for further analysis. At the same time the plasma or serum is protected from the environment reducing the risk of plasma or serum getting lost or spoiled.

In one embodiment the plasma or serum separator is formed as a strip, wherein the plasma or serum collecting cavity if formed within the strip. A plasma or serum separator formed as a strip with the collecting cavity integrated into the strip provides a separator which is easy to handle and which can be manufactured easily at low costs.

In an embodiment the plasma or serum collecting cavity is fixed and/or covered by the holding member. Fixing and/or covering the collecting cavity by the holding member facilitates the integration of the collecting cavity into the separator and thereby reduces the costs of manufacture. The holding member may be laminated or glued to the blood separation member.

In an embodiment the plasma or serum collecting cavity is confined at least partially by a transparent material allowing electromagnetic radiation to pass though the cavity and though the plasma or serum collected in the cavity. Confining the collecting cavity securely encloses the plasma or serum within the cavity so that no plasma or serum gets lost. Using a transparent material for the confinement allowing electromagnetic radiation to pass though the cavity and though the plasma or serum collected in the cavity allows to perform photometric measurements to be carried out on the plasma or serum without extracting the plasma or serum from the collecting cavity. Instead, the plasma or serum separator with the plasma or serum collected in the cavity may be arranged in a photometer in order to carry out the measurement. This facilitates the handling and prevents any plasma or serum from being lost or spoiled, since no plasma or serum has to be transferred from the separator to an additional analysis device.

In a particular embodiment the transparent material is transparent for electromagnetic radiation in the rage of 380 nm to 780 nm and more particular for electromagnetic radiation in the rage 450 nm to 460 nm. 380 nm to 780 nm is the range of the visible light, which is commonly used for photometric measurements, and 450 nm to 460 nm is the range which is typically used to determine the bilirubin concentration in the plasma or serum.

In a further embodiment the plasma or serum collecting cavity is at least partially open so that it is freely accessible from at least one side. Such an opening allows electrodes to be inserted into the collecting cavity in order to enable conductive measurements of the plasma or serum collected in the cavity.

Alternatively the cavity is completely closed and the electrodes may be pierced through the cover into the cavity. This provides the advantage that the plasma or serum is sealingly enclosed within the cavity before the electrodes are inserted. Thus, the plasma or serum is isolated from the environment avoiding any possible pollution. The separator may be transported even by mail without the risk of the plasma or serum getting spoiled or lost.

In a further embodiment the plasma or serum collecting cavity is provided with at least one electrode which is configured to contact the plasma or serum collected in the cavity. This avoids the need for introducing external electrodes into the cavity and facilitates the performance of a conductive measurement.

In an embodiment the plasma or serum separator is provided with an integrated circuit connected to the electrodes. The integrated circuit may be configured to analyze the plasma or serum collected in the cavity.

An integrated circuit combined with the separator allows the analysis of the plasma or serum to be carried out by the separator itself without the need for an additional analysis device. This reduces the cost for the analysis, as the costs for the additional (external) analyses device may be saved. Furthermore, the analysis can be carried out everywhere, even mobile, as there is no need to transfer the plasma or serum from the separator to an analysis device. Instead, the analysis is performed by the separator itself.

In an embodiment the plasma or serum separator comprises a plurality of plasma or serum collecting cavities.

The plasma or serum collecting cavities may be connected individually and in parallel to the plasma or serum sampling aperture. Alternatively or additionally at least some of the plasma or serum collecting cavities may be connected serially to each other.

A plurality of collecting cavities allows to perform a number of different measurements on the same sample of blood introduced into the separator. Thus, a number of different measurements may be carried out in short time.

Connecting the cavities individually to the sampling aperture ensures that all cavities are supplied with "fresh" plasma or serum from the sampling aperture at the same time. Connecting the cavities serially ensures that the cavities are filled with plasma or serum in a predetermined order.

In an embodiment the plasma or serum collecting cavities are formed circular, elliptical, angular, in particular triangular, rectangular, hexagonal, octagonal, polygonal, or any combination thereof. Thus, the form of the cavities may be chosen in order to match the specific need of the measurement (s) to be carried out. In particular, the form of the cavity may be adjusted to the optic of the photometer and/or the form of the electrodes to be introduced into the cavity.

In an embodiment the plasma or serum separator comprises a reagent in at least one of the collecting cavities. This allows a reaction of the plasma or serum with a specific reagent in preparation of the measurement and avoids the need of manually adding the reagent to the plasma or serum. Reagent being present in the cavity facilitates the handling and avoids errors which may arise from adding the wrong or no reagent at all to the plasma or serum.

Alternatively the plasma or serum sampling method may comprise the step of adding a reagent to the plasma or serum in said collecting cavity. This is in particular advantageous when the cavity is open so that no fluid reagent may be stored in the cavity. Furthermore, it provides more flexibility, as the reagent needs not to be chosen when the separator is produced but may by selected at the time the measurement is carried out.

If the separator comprises a plurality of cavities a different reagent may be added to each of the cavities in order to cause different chemical reactions to take place and to perform different tests on the plasma or serum collected in the cavities.

The plasma or serum sampling method of the invention may further comprise the step of sampling the plasma or serum into the plasma or serum collecting cavity by squeezing the plasma or serum out of the blood separation member. Squeezing the plasma or serum out of the blood separation member is a very efficient method of transferring the plasma or serum from the blood separation member to the collecting cavity.

The invention also comprises a method for analyzing plasma or serum comprising the steps of
   sampling plasma or serum according to the invention;
   passing electromagnetic radiation though the cavity and the plasma or serum collected in said cavity and
   measuring the absorption caused by the plasma or serum in said cavity.

The invention also comprises a method for analyzing plasma or serum comprising the steps of
   sampling plasma or serum according to the invention;
   contacting the plasma or serum collected in the cavity with at least two electrodes; and
   measuring the conductance of the plasma or serum collected in said cavity.

The electrodes may be integrated into the cavity at the time of manufacture, introduced through an opening of the cavity or pierced through the cover of the cavity.

The analyzing methods described before provide reliable and convenient methods for analyzing plasma or serum, as there is no need to transfer the plasma or serum to an external analysis device so that any disadvantages and risks which are connected to such a transfer can be avoided.

Embodiments of the invention will be described in the following with reference to the figures, wherein FIG. 1 is schematic descriptive view showing one example of a bilirubin analyzer for exclusive capillary tube use;

Figure 1:
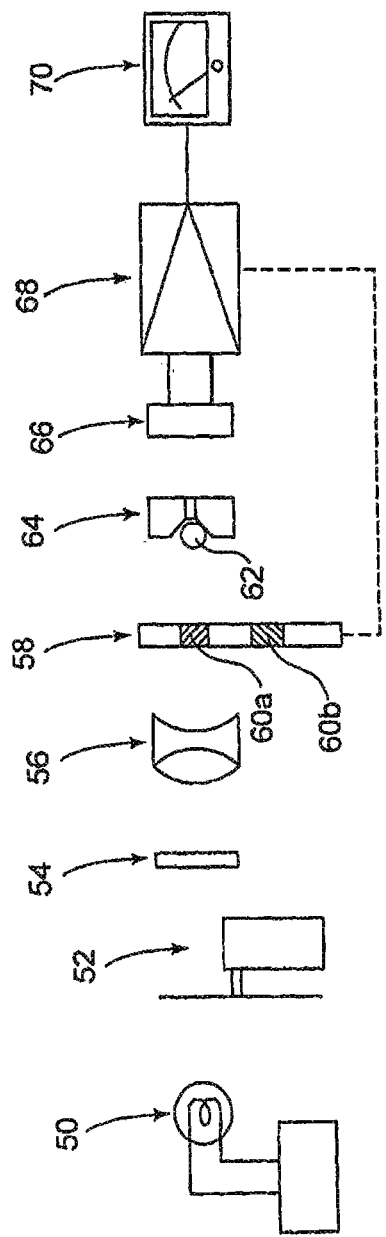

FIG. 1 shows a photometer for measuring a bilirubin concentration of a neonate is such that a blood-sampling needle is stuck in a sole of the neonate to sample blood with a capillary tube. Sampled blood is separated to obtain serum or plasma by a centrifuge for capillaries and a bilirubin concentration is attained by conversion of an absorbance in the proximity of a wavelength in the range of from 450 to 460 nm, which is a bilirubin absorption wave length. In order to perform the examination, a centrifuge for exclusive use has been required and a time has been consumed in separating operation longer than in measurement itself.

In FIG. 1, reference numeral 50 designates a light source; 52, a optical light chopper; 54, a heat absorbing filter; 56, a lens; 58, a filter disk; 60a and 60b, interference filters; 62, a capillary tube; 64, a capillary tube holder; 66, a photodiode; 68, an amplifier; and 70, a meter. The capillary tube 62 in which plasma or serum isolated from blood is accommodated is to be held on the capillary tube holder 64 and light from the light source 50 is to be passed through the optical light chopper 52, the heat absorbing filter 54, the lens 56 and the interference filters 60a and 60b and is irradiated to the capillary tube 62, thereby an absorbance being measured at a wavelength in the proximity of a value in the range of from 450 to 460 nm with the photodiode 66 to detect a bilirubin concentration with the meter 70.

Figure 2:
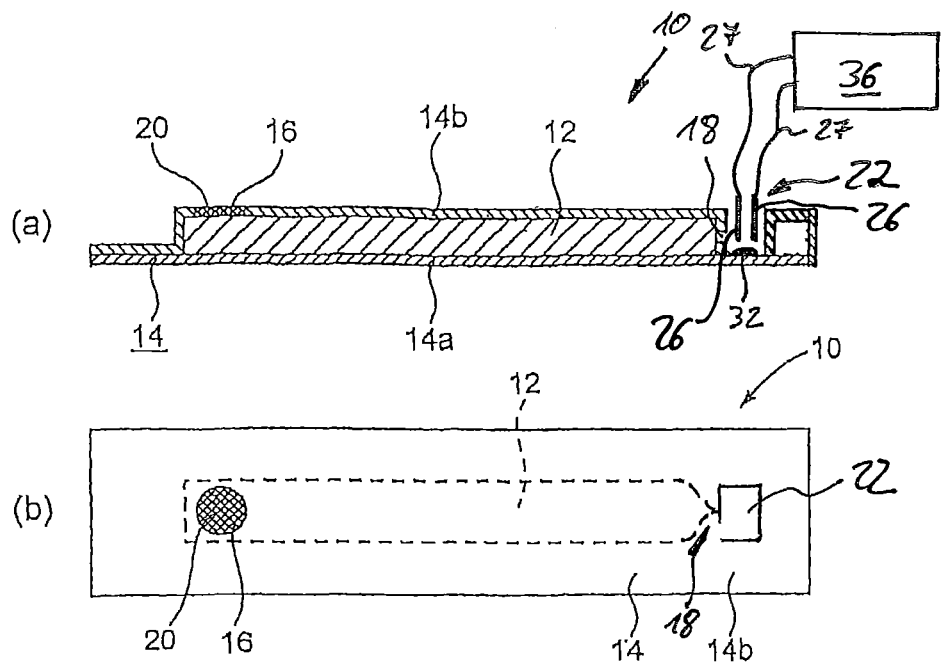
FIG. 2 shows a first embodiment of a plasma or serum separator of the present invention, wherein the part (a) is a schematic sectional view thereof and the part (b) is a schematic top plan view thereof.

FIG. 2 shows a first embodiment of a plasma or serum separator according to the present invention, wherein the FIG. 2(a) shows a schematic sectional view thereof and FIG. 2(b) shows a schematic top plan view thereof.

In FIG. 2 reference numeral 10 designates a plasma or serum separator according to the present invention. The plasma or serum separator 10 has a blood separation member 12 covered and held by a holding member 14. The holding member 14 includes a base film member 14a on the lower side and a covering film 14b on the upper side. The blood separation member 12 is fixedly sandwiched between the base film 14a and covering film 14b. When fixedly covering and holding the blood separation member 12 with the holding member 14, by adhering them without leaving any clearance there between, it is possible to isolate high purity plasma or serum from whole blood. The holding member 14 may be laminated or glued to the separation member 12 in order to provide a strong and permanent bonding between the holding member 14 and the separation member 12.

A blood introducing portion 16 is formed on the upper surface of a first (left) end portion of the covering film 14b and a plasma or serum sampling aperture 18 is perforated at a second (right) end portion of the separation member 12.

The sampling aperture 18 is preferably a circle with a diameter in the range from 0.02 mm to 1 mm or a square equivalent thereto. The method of forming the plasma or serum sampling aperture 18 is not specifically limited and the aperture 18 is preferably formed by perforating the covering film 14b covering the blood separation member 12 using a needle-like tool such as a syringe needle.

A collecting cavity 22 is formed next to the sampling aperture 18 opposite to the blood separation member 12, the collecting cavity 22 being defined by the base film member 14a at its bottom and the covering film 14b at its sides. The collecting cavity 22 is open, i.e. without a cover at its top.

After blood has been introduced into the blood separation member 12 via the blood introducing portion 16 and the plasma or serum has been separated from the blood cells by the blood separation member 12, the plasma or serum is extracted from the blood separation member 12, e.g. by applying pressure to the blood separation member 12 in order to squeeze out the plasma or serum. The plasma or serum, which has been squeezed out from the blood separation member 12 is collected in the collecting cavity 22 for further analysis.

Possible methods for squeezing out the plasma or serum from the blood separation member 12 into the collecting cavity 22 are described in detail below with reference to FIGS. 9 to 11.

Portions of the holding member 14 confining the collecting cavity 22 may by coated with a reagent 32, the reagent 32 to be dissolved by the plasma or serum entering the collecting cavity 22 and reacting therewith. Coating portions of the collecting cavity 22 with a reagent 32 provides a reliable and convenient way of adding a reagent 32 to the plasma or serum in preparation of the following measurements. Alternatively or additionally a fluid reagent may be filled into the cavity 22.

Electrodes 26 connected by electrical conductors 27 to an external analysis device 36 may by inserted into the collecting cavity 22 via its open top side in order to measure the electrical conductivity of the plasma or serum collected in the collecting cavity 22.

Reference numeral 20 designates a network member covering the blood introducing portion 16. Since the blood separation member 12 exposed to the outside at the blood introducing portion 16 is covered with provision of the network member 20, the blood separation member 12 is protected from damage or the like. Any material may be used as the network member 20 as far as it does not become spherical by the action of surface tension as a result of blood permeation, in particular a plastic material such as nylon may be used.

The shape of the blood introducing portion 16 is not specifically limited and may be either a circle as shown in FIG. 2(b) or any of other shapes such as polygons.

Figure 3:
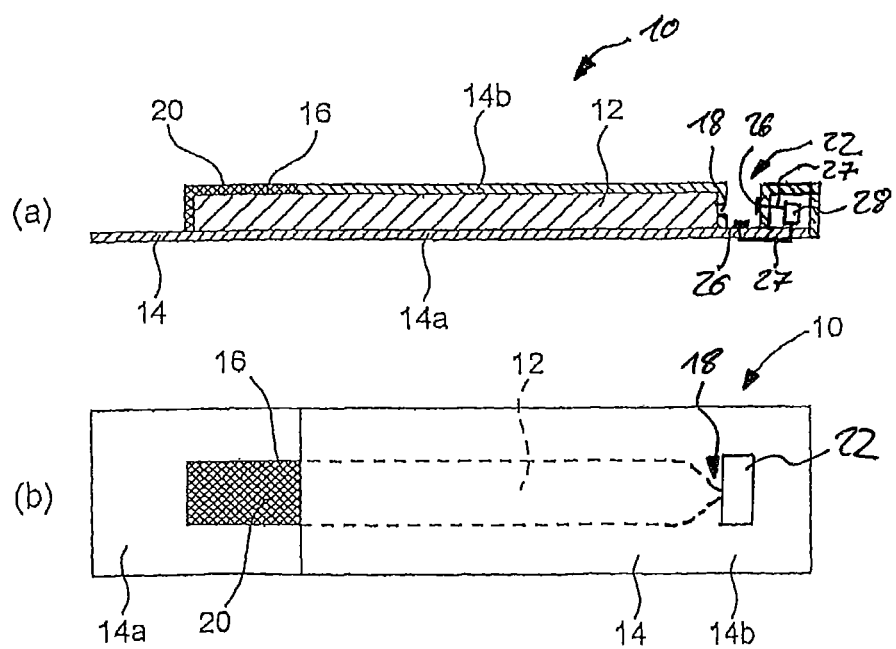
FIG. 3 shows a second embodiment of a plasma or serum separator of the present invention, wherein the part (a) is a schematic sectional view thereof and the part (b) is a schematic top plan view thereof.

For example, as shown in FIG. 3 for a second embodiment of the present invention, the shape of the blood introducing portion 16 can also be formed in such a way that the first end portion of the covering film 14b is all peeled off to form a large opening portion.

Although the blood introducing portion 16 is preferably covered by the network member 20 in FIGS. 2 and 3, the function and result of the present invention can be achieved even in a state where the blood separation member 12 is exposed to the outside air without providing the network member 20.

In the second embodiment shown in FIG. 3 electrodes 26 are integrated into the collecting cavity 22 and connected via electrical conductors 27 to an integrated circuit 28, which is attached to or integrated into the holding member 14.

An electronic circuit 28, which is integrated into the separator 10 allows the analysis of the plasma or serum to be carried out by the separator 10 itself without the need for an external analysis device 36. This reduces the cost for the analysis as the costs for the external analyses device 36 may be saved. Furthermore, the analysis can be carried out everywhere and even mobile as there is no need to transfer the plasma or serum or the separator 10 comprising the plasma or serum to an analysis device 36.

The separator 10 of the first embodiment shown in FIG. 2 may be provided with internal electrodes 26 and an integrated circuit 28 as shown by example for the second embodiment in FIG. 3, as well.

Figure 4:
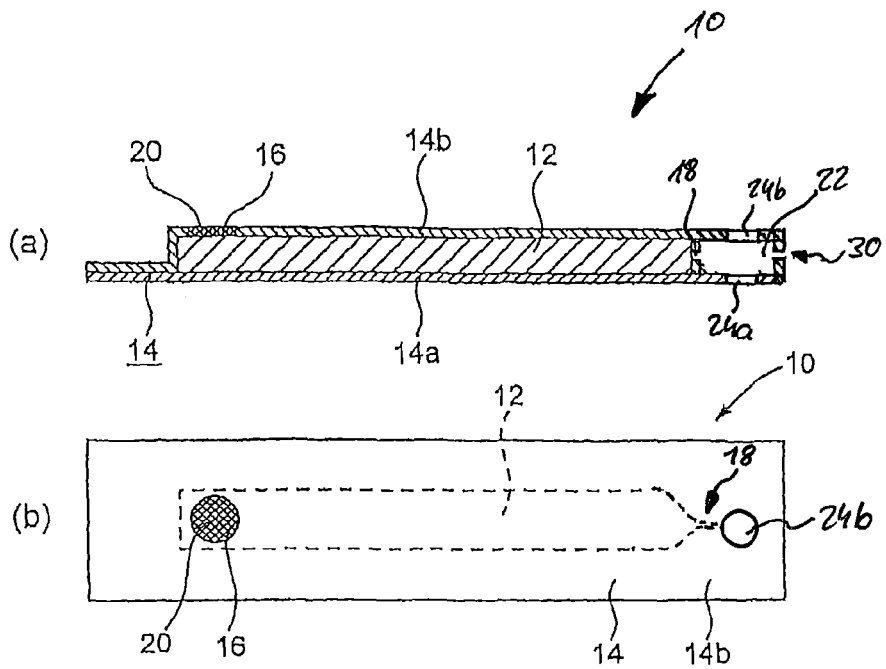
FIG. 4 shows a third embodiment of a plasma or serum separator of the present invention, wherein the part (a) is a schematic sectional view thereof and the part (b) is a schematic top plan view thereof.
Figure 5:
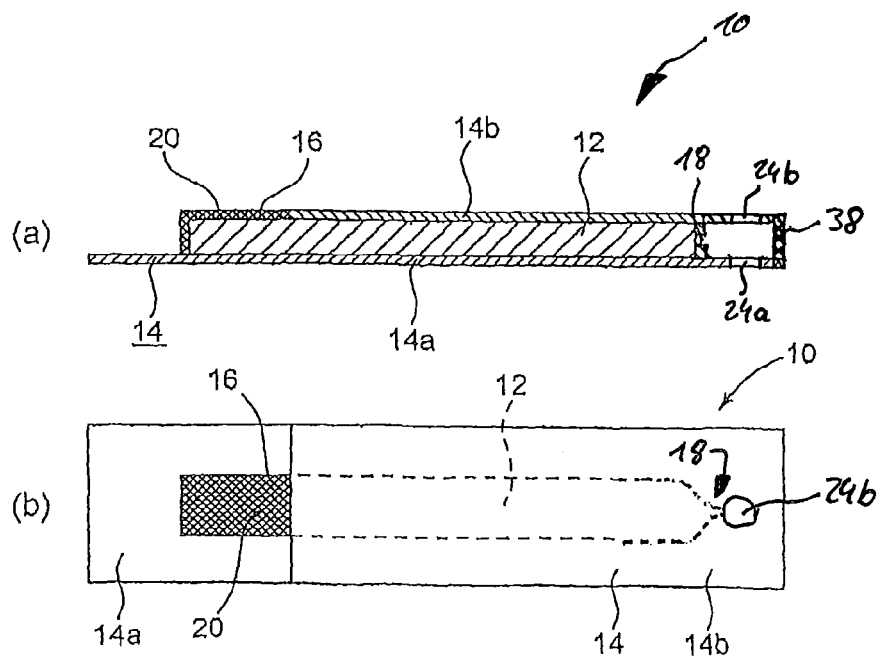
FIG. 5 shows a fourth embodiment of a plasma or serum separator of the present invention, wherein the part (a) is a schematic sectional view thereof and the part (b) is a schematic top plan view thereof.

FIGS. 4 and 5 respectively show a third and fourth embodiment of the separator 10 according to the invention.

In the third and fourth embodiment the collecting cavity 22 is completely encased by the holding member 14. The base film 14a and the covering film 14b forming the holding member 14 are respectively provided with a transparent portion 24a, 24b allowing electromagnetic radiation to pass through the collecting cavity 22 and any plasma or serum collected in the collecting cavity 22 in order to allow photometric measurements to be carried out on the plasma or serum collected in the collecting cavity 22.

The transparent portions 24a, 24b are preferably transparent for electromagnetic radiation in the range comprising visible light, but they may be chosen to be transparent for any radiation used for photometric measurements including infrared and ultraviolet radiation, as well.

A separator 10 according to the third or fourth embodiment may be introduced instead of the capillary tube 62 into a photometer as shown in FIG. 1 in order perform photometric measurements. In this case, the plasma or serum is transferred from the separation member 12 to the collecting cavity 22 by squeezing the plasma or serum out of the separation member 12 either before or after the separator 10 has been introduced into the photometer.

In the third embodiment shown in FIG. 4 a venting aperture 30 is provided to enable air, which is present in the collecting cavity 22, to leave the collecting cavity 22 in order to avoid an increase of pressure in the collecting cavity 22 which may prevent plasma or serum from entering into the collecting cavity 22.

The venting aperture 30 is preferably dimensioned so that it allows air to leave the collecting cavity 22 but does not allow plasma or serum to leave the collecting cavity 22 via the venting aperture 30. Of course, a plurality of venting apertures 30 may be provided, as well.

In the fourth embodiment shown in FIG. 5 no venting aperture 28 is formed, but portions of the holding member 14 next to the collecting cavity 22 are made of a membrane 38 which is permeable for air but not for plasma or serum in order to allow air to leave the collecting cavity 22.

A venting aperture 30 as shown in FIG. 4 may be applied also to the fourth embodiment shown in FIG. 5 and the membrane 38 shown in FIG. 5 may be used in addition or as alternative to the venting aperture 30 of the third embodiment shown in FIG. 4.

A fluid or solid reagent 32, which is not capable of escaping from the collecting cavity 22 via the venting aperture 30 or the membrane 38 may be present in the collecting cavity 22 in order to react with the plasma or serum entering the collecting cavity 22 in preparation of the measurement. This provides a reliable and convenient way of adding a reagent 32 to the plasma or serum in preparation of the following measurement and avoids any errors which may be caused by a manual addition of the reagent 32.

Of course, the collecting cavities 22 according to the third and fourth embodiments shown in FIGS. 4 and 5 may by provided with internal electrodes 26 and an integrated circuit 28 as shown by way of example for the second embodiment in FIG. 3, as well.

FIGS. 6(a)-6(i), 7(a), 7(b) and 8 respectively show top views of possible further embodiments of a plasma or serum separator 10 according to the invention. In these top views the covering film 14b of the holding member 14 has been removed in order to show the blood separation member 10 and fluid channels 23 connecting the cavities 22 to each other and to the sampling aperture 18.

FIGS. 6(a)-6(i) in particular show various possible shapes of the collecting cavity 22.

The blood separation member 12 of the separators 10 shown in FIGS. 6(a)-6(i) comprises an end portion 12a next to the sampling aperture 18, which is narrower in shape than the portion of the separation member 12 next to the introducing portion 16. Such a tapered shape of the separation member 12 makes it easier to separate the red blood cells from the plasma or serum.

Figure 6A:
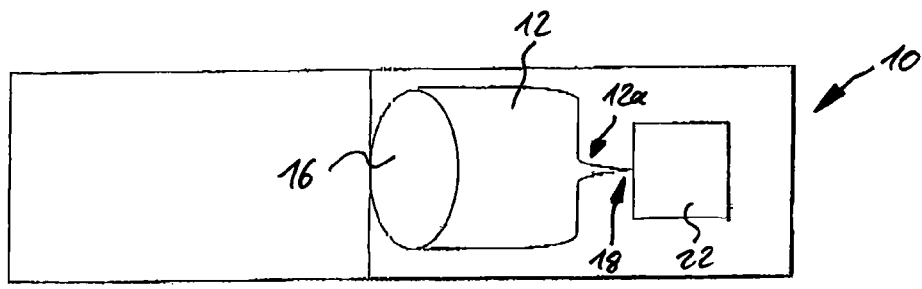
FIGS. 6a-6i, 7a, 7b and 8 show top views of possible further embodiments of a plasma or serum separator according to the invention.

In its most simple form the collecting cavity 22 may be quadratic when viewed from above (FIG. 6(a)). Alternatively the collecting cavity 22 may be formed rectangular with the longer side of the rectangle being arranged orthogonal (FIG. 6(b)) or parallel (FIG. 6(c)) to the longitudinal extension of the rectangular formed separator 10.

Figure 6B:
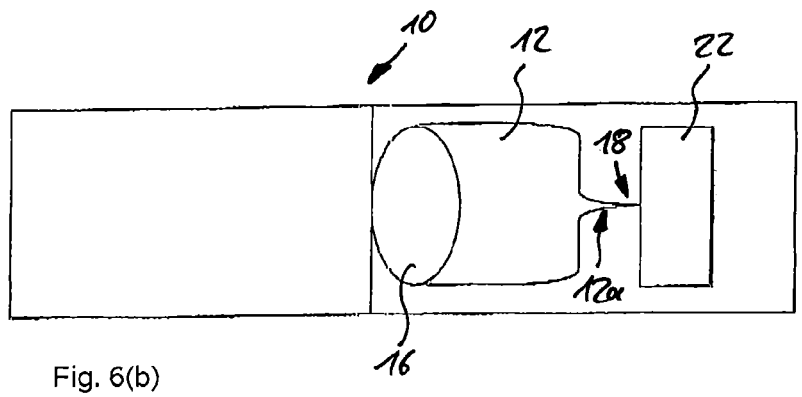
Figure 6C:
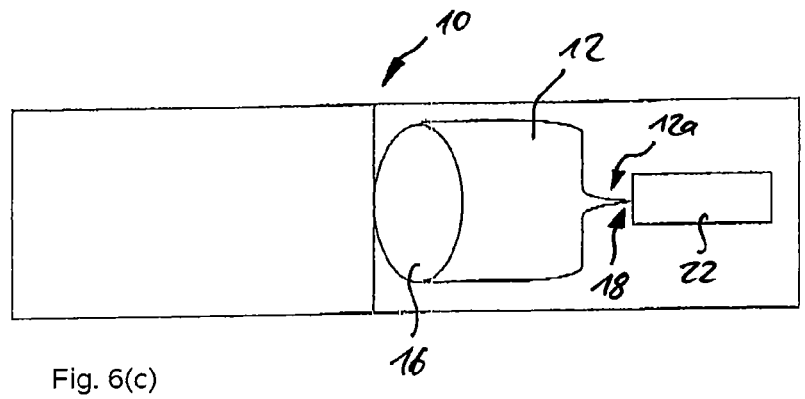
Figure 6D:
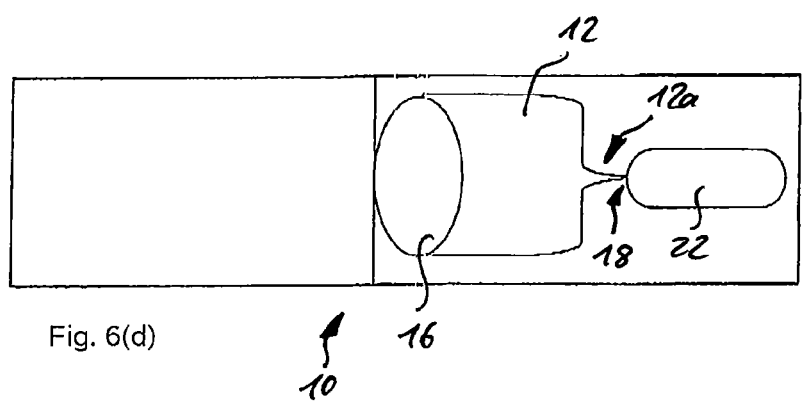

In a further embodiment (FIG. 6(d)) the edges of the rectangular (or square) are rounded down. Of course this may also apply to a rectangular which is arranged orthogonal to the longitudinal extension of separator 10 as shown in FIG. 6(b).

Figure 6E:
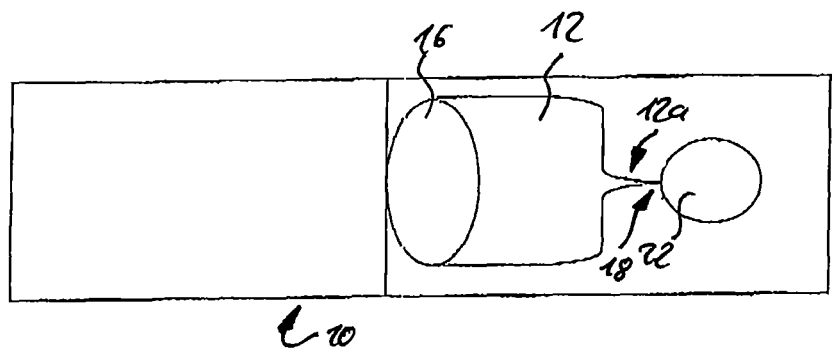

In another embodiment (FIG. 6(e)) the collecting cavity 22 has a circular or elliptical form.

Figure 6F:
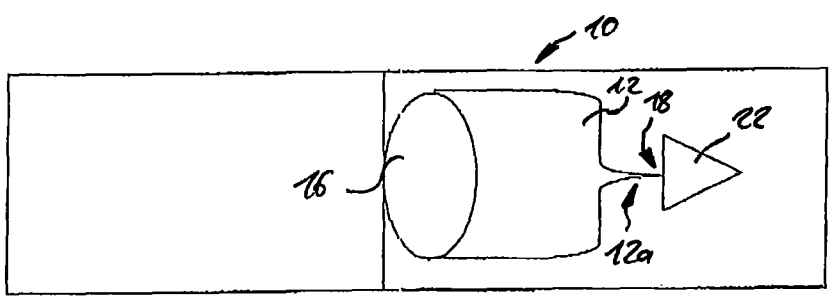
Figure 6G:
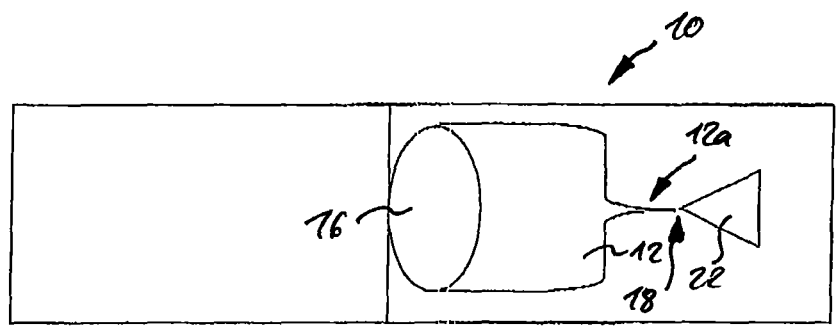

The collecting cavity 22 may also be formed as a triangle with one of its corners oriented to (FIG. 6(g)) or facing away (FIG. 6(f)) from the sampling aperture 18 formed at the end of the blood separation member 12.

Figure 6H:
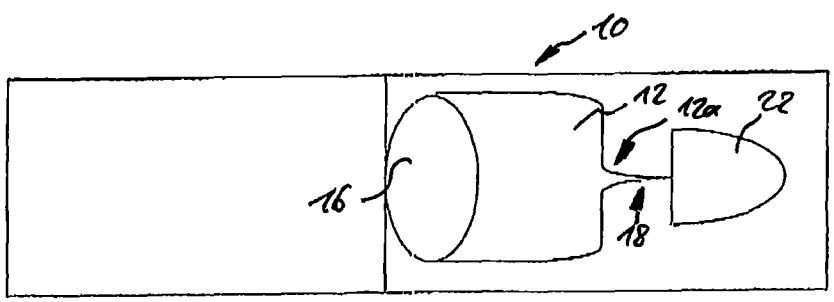
Figure 6I:
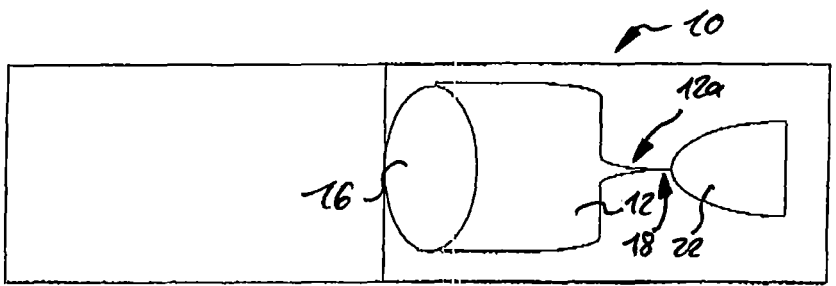

The edges of the triangle may be rounded down, as well, resulting in a half elliptical or half circular shape of the collecting cavity 22 (FIGS. 6(h) and 6(i)).

Of course, the shapes of the cavities 22 shown in FIGS. 6(a)-6(i) are only examples and alternative shapes of the collecting cavity 22, which are easy to produce and/or are adjusted to the optics of a photometer to be used for analyzing the plasma or serum collected within the collecting cavity 22 of the separator 10, may be formed.

Figure 7A:
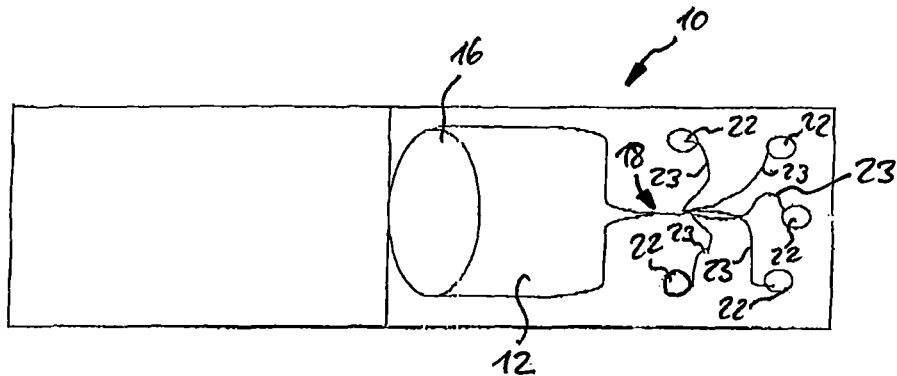
Figure 7B:
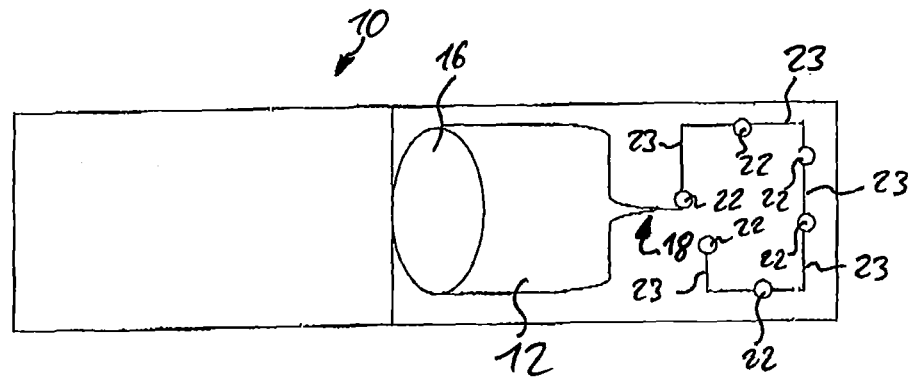

FIGS. 7(a) and 7(b) respectively show exemplary embodiments of a separator 10 according to the invention comprising a plurality of collecting cavities 22.

The embodiment shown in FIG. 7(a) comprises five cavities 22, which are individually and separately connected to the sampling aperture 18 by individual fluid channels 23. Thus, plasma or serum leaving the blood separation member 12 via the sampling aperture 18 will flow in parallel through each of the fluid channels 23 into each of the cavities 22 filling the cavities 22 independently of each other.

In an alternative embodiment shown in FIG. 7(b) six cavities 22 are formed and serially connected to each other by fluid channels 23 so that the cavities 22 will fill up sequentially one after the other. Any reagent 32 being present in the first collecting cavity 22 next to the sampling aperture 18 will be transferred by the plasma or serum to each of the following cavities 22. Thus, this configuration allows the distribution of a reagent 23 from one cavity 22 to the other following cavities 22.

It will depend on the kind of analysis to be performed if the embodiment comprising parallel connected cavities 22 according to FIG. 7(a) or the embodiment comprising cavities 22 which are serially connected according to FIG. 7(b) is preferred.

It is to be noted that the number of five (FIG. 7(a)) or six (FIG. 7(b)) cavities 22 is only chosen as an illustrative example and that any number of cavities 22, which is useful for the intended purpose, may be formed.

Figure 8:
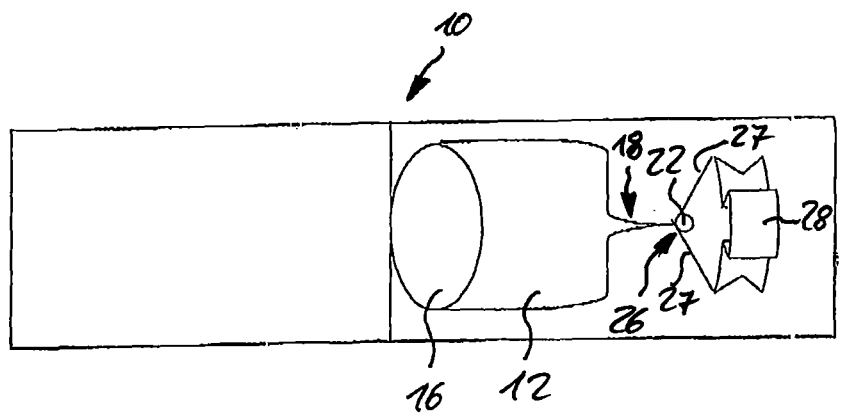

FIG. 8 shows a further example of a separator 10 according to the invention comprising a single circular collecting cavity 22 provided with two electrodes 26. The electrodes 26 are connected by electrical conductors 27 to an electronic circuit 28 which is arranged in or at the holding member 14.

A separator 10 according to the embodiment shown in FIG. 8 allows to measure the conductivity of the plasma or serum supplied to the collecting cavity 22 without the need for an external device and/or applying external electrodes to the collecting cavity 22. This facilitates the measurement of the conductivity of the plasma or serum separated by the blood separation member 20 and collected in the collecting cavity 22.

The blood separation member 12 may comprise fibrous materials and/or porous materials which may include: inorganic fibers such as glass fibers and asbestos; natural organic fibers such as cotton, pulp, silk and the like; semi-synthetic fibers or synthetic fibers such as cellulose, cellulose acetate, polyester, polypropylene, polyurethane, polyamide, polyvinyl formal, polyethylene, polyvinyl chloride, viscose rayon and the like.

A glass fiber filter is preferably made of borosilicate glass with an average pore size in the range of from 3 to 6 μm and a preferable glass fiber membrane with the specification available on the market is of the GF/D type (manufactured by Whatman Inc.)

There may be included in the plasma or serum separation member 12 either alone or jointly red blood aggregating materials, for example, known red blood cell aggregating materials such as cation polymer, lectin, an antibody for red blood cells and the like.

As the blood separation member 12, there are preferably used materials containing the fibrous materials and/or porous materials coated with coating materials such as hexylene glycol, propanol with a butoxy group and acrylamide with a butoxy group. The coating materials may be used either alone or jointly of two or more kinds. Especially, as a glass fiber filter, it is preferably used glass fibers coated with one kind or two or more kinds selected from the group consisting of hexylene glycol, propanol with a butoxy group and acrylamide with a butoxy group.

By using glass fibers coated with hexylene glycol; and/or a butoxypropanol, for example, 1-butoxy-2-propanol, which is a propanol with a butoxy group as a functional group; and/or a butoxymethylacrylamide, for example, N-butoxymethyl acrylamide, which is an acrylamide with a butoxy group, hemolysis in a separation process can be restricted to a practically non-problematical amount and separation of plasma or serum from red blood cells starts simultaneously with dropping of blood, thereby quick separation being realized.

A coating amount of hexylene glycol; and/or a propanol with a butoxy group; and/or an acrylamide with a butoxy group relative to glass fibers is 0.05 wt %, preferably 0.1 wt % and more preferably 0.2 wt % as the lower limit and 3.0 wt %, preferably 2.0 wt % and more preferably 1.5 wt % as the upper limit.

As a method of coating glass fibers with a red blood cell aggregating material, a method is preferable in which a blood separation member 12 made of glass fiber filter is impregnated with a coating material in solution and the impregnation is, for example, conducted by applying an impregnating solution to a glass fiber filter or immersing it in the solution.

An amount of an impregnating solution is preferably in the range of from 0.3 wt %) to 2.0 wt % and if the amount exceeds the range, a capillary force between the glass fibers is affected to release hemoglobin from red blood cells in hemolysis and extend a delay time for development of blood.

A preferable method in which the glass fiber filter is coated with hexylene glycol; and/or a propanol with a butoxy group; and/or an acrylamide with a butoxy group is such that a glass fiber filter paper is immersed in an impregnating solution including hexylene glycol, N-butoxymethyl acrylamide or 1-butoxy-2-propanol and then taken out, followed by desiccating it at a temperature in the range of from room temperature to 90° C. A desiccating time is in the range of from 25 to 80 min at a temperature in the range of from 50° C. to 90° C., which is practically non-problematical.

The size of the blood separation member 12 is required to be at least of a volume corresponding to the blood sample amount. The shape thereof is not specifically limited and may be any selected from the group consisting of a quadrangle, a triangle, other polygons, a circle, an ellipse, a shape of a tapered battledore plate with a narrower distal end 12a and the like.

While preferably the shape of a box as shown in FIGS. 2 to 5 is used, a blood separation member 12 whose distal end portion 12a next to the sampling aperture 18 is narrower in shape as shown in FIGS. 6(a) to 6(i) is preferable because of easiness with which red blood cells are separated from plasma or serum. As to the thickness of the blood separation member 12 there is a necessity that in order to separate a blood cell portion from a plasma or serum portion in whole blood, the blood cell portion is caused to remain in the blood separation member 12 in whole blood supplied from the blood introducing portion 16, and the plasma or serum portion is caused to migrate in a traverse direction, that is in a direction toward the plasma or serum sampling aperture 18, and hence the thickness of the blood separation member 12 is set such that the blood separation member 12 is filled with the blood cell portion from the upper surface to the bottom surface thereof and plasma or serum flows in the traverse direction in the blood cell separation member 12. The size of the blood separation member 12 has only to be properly determined based on an amount of plasma or serum necessary for an examination without a specific limitation thereon.

In a case where a blood sampling needle is stuck in a hand, a foot or the like to sample blood, a blood amount that can be sampled is in the range of from about 25 to about 100 μL and a thickness and other dimensions are properly determined according to a blood amount to be sampled. For example, in a case of a blood amount of 25 μL, the thickness is preferably in the range of from 0.1 to 0.6 mm and in a case of a blood amount of 100 μL, the thickness is preferably in the range of from 0.1 to 1.4 mm.

The holding member 14 may be any of members capable of covering the surfaces of the blood separation member 12 without leaving any clearance and having a liquid non-penetrating property. The covering film 14b in at least a region at the distal end of the holding member 14 where plasma or serum is isolated has to be soft so as to enable blood to be pushed out. It is preferable to use a transparent or semi-transparent, liquid non-penetrating film as the holding member 14 because migration of blood and isolation of plasma or serum can be confirmed. The base film 14a and covering film 14b may be either the same material as or different from each other. As the holding member 14, preferably used is, for example, a pressure sensitive adhesive tape obtained by coating a pressure sensitive adhesive on a plastic film. The following plastic films can be used either alone or jointly: polyester film such as polyethylene terephthalate, polypropylene, polyethylene, polyvinyl chloride and the like. A thickness of the holding member 14 is not specifically limited and preferably on the order of 100 μm.

A plasma or serum separator 10 according to the invention can be fabricated in a way described below and used.

A glass fiber filter paper GF/D (manufactured by Whatman Inc. with a thickness of 0.2 mm, and an average pore size of 5.7 μm) cut into a size of 10 mm in width and 20 mm in length was immersed in a 0.05% aqueous solution of N-butoxymethyl acrylamide (manufactured by Wako Pure Chemical Industries Ltd.) and thereafter, the glass fiber filter cut was desiccated at a temperature of 70 DEG C. for 30 min to thus prepare a blood separation member 12.

A polypropylene plastic film (with a thickness of 100 μm) on which a pressure sensitive adhesive was applied was used as a holding member 14. Both surfaces of the blood separation member 12 were adhered with a base film 14a with a size of 20 mm×30 mm and a covering film 14a with a size of 20 mm×15 mm, respectively, leaving a size of 10 mm×10 mm as a blood introducing portion. In an embodiment the base film 14a and the covering film 14b are laminated to the blood separation member 12 and to each other in order to form a separator 10 according to the invention.

Thereafter a portion of the covering film 14 was perforated with a syringe needle (22 G diameter) to form a plasma or serum sampling aperture 18, and thus a plasma or serum separator 10 was fabricated. That is, the fabricated square plasma or serum separator 10 was 10 mm×20 mm square having a blood separation member 12 covered with a plastic film, which includes a blood introducing portion 16 with an opening of 10 mm×10 mm square at a first end portion of the upper surface thereof, a plasma or serum sampling aperture 18 with 22 G diameter at a second end portion of the side surface thereof, and a plasma and serum collecting cavity 22 formed on the other side of the sampling aperture 18 opposite to the separation member 12.

Figure 9:
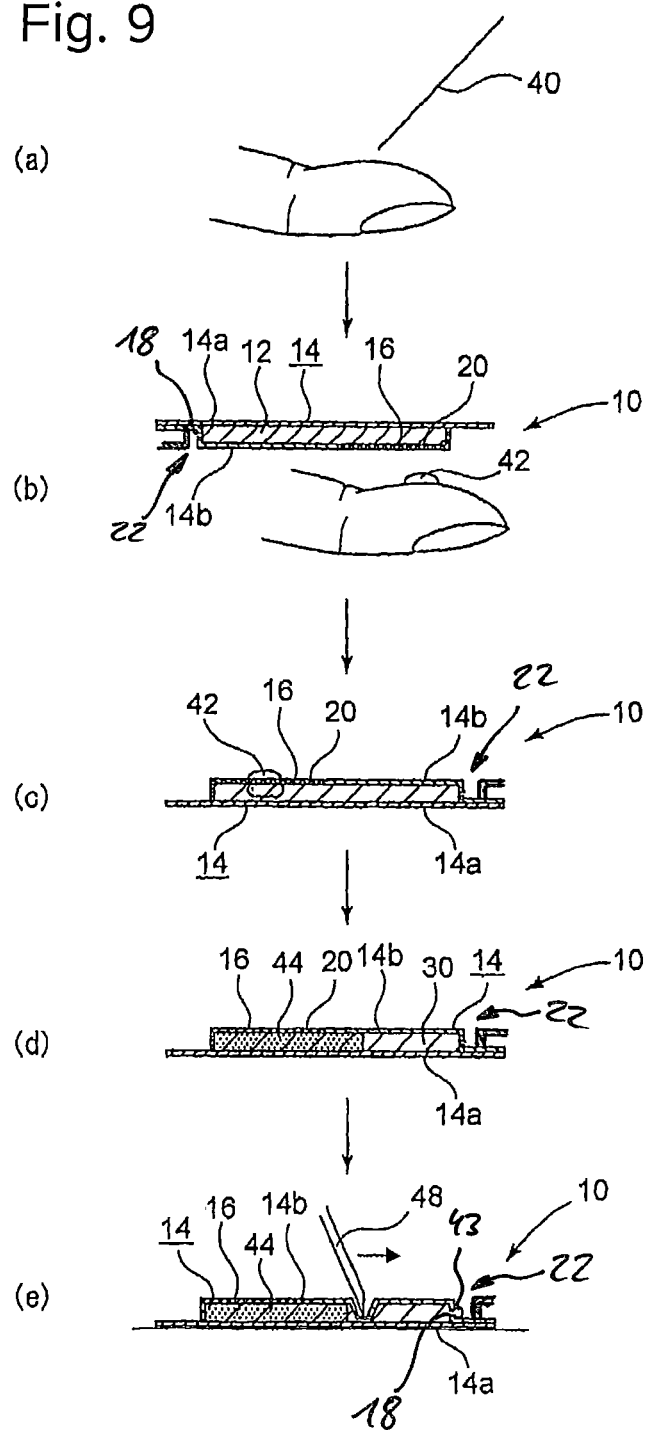
FIG. 9 is a descriptive schematic view showing one embodiment of a process for extracting plasma or serum from the blood separation member.
Figure 10:
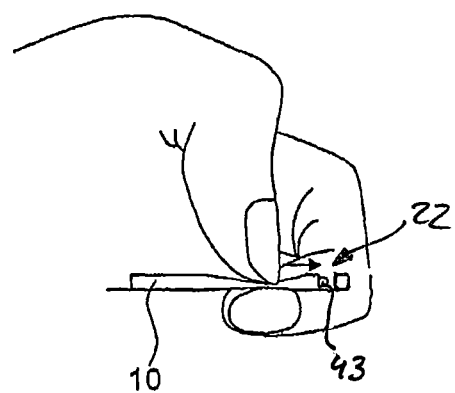
FIG. 10 is a descriptive schematic view showing another embodiment of a process extracting plasma or serum from the blood separation member.
Figure 11:
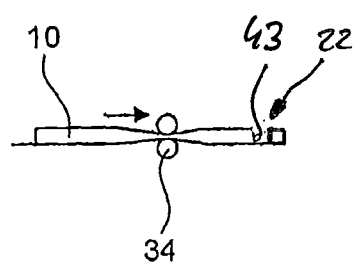
FIG. 11 is a descriptive schematic view showing yet another embodiment of a process for extracting plasma or serum from the blood separation member.

FIGS. 9 to 11 show possible examples for squeezing the plasma or serum from the blood separation member 12 into the collecting cavity 22.

In the first aspect a lancing device, for example a lancet 40, is at first stuck in a blood sampling portion to cause the portion to bleed (FIG. 9(a)). The blood sampling portion is not specifically limited and for example, a hand, a foot or the like is preferably selected. After the bleeding, the blood introducing portion 16 or the network member 20 of the plasma or serum separator 10 of the present invention is brought into contact with the bleeding site to sample blood 42 and to supply the blood 42 through the blood introducing portion 16 (FIGS. 9(*b*), 9(*c*)).

In this case, the blood separation member 12 covered with the holding member 14 does not absorb any more of the blood after the blood separation member 12 is filled with plasma or serum isolated from red blood cells even if the blood 42 is further supplied.

The absorbed blood 42 migrates in the blood separation member 12 from the blood introducing portion 16 to the plasma or serum sampling aperture 18 at the distal end portion and a difference in migrating speed between plasma or serum and red blood cells is used so that red blood cells 44 is isolated in the blood introducing portion 16 side while plasma or serum 43 is isolated in the plasma or serum sampling aperture 18 side; thereby plasma or serum being isolated in the blood separation member 12 (FIG. 9(*d*)). With the holding member 14, especially the covering film 14*b* being transparent or semi-transparent, the separation process can be visually confirmed through the covering film 14*b*. A sampling amount of plasma or serum is determined by a hematocrit value of the blood and a plasma or serum separation ability of the blood separation member 12, and for example, in a case of a blood amount of 25 μL, plasma or serum in the range of from 5 to 12 μL flows from the blood introducing portion 16 in the traverse direction, that is in a direction toward the plasma or serum sampling aperture 18, in a time in the range of from 40 to 180 sec, during which separation is effected.

The isolated plasma or serum 43 can be squeezed out through the plasma or serum sampling aperture 18 formed at the distal end portion into the collecting cavity 22 (FIG. 9(*e*)).

As shown in FIG. 9(*e*), by pressing the holding member 14 in the plasma or serum side of the boundary between the blood 44 and the plasma or serum 43 in the direction of the plasma or serum sampling aperture 18 side from the blood introducing portion 16 side using a tool 48, a finger or the like, plasma or serum can be easily discharged.

Various kinds of sampling methods of plasma or serum 43 are conceived in addition to the methods described above and, for example, as shown in FIG. 10, a method can be adopted in which in the state that the upper surface and bottom surface are pressed with fingers without using a pressing device, by moving a fingernail in the direction shown by an arrow, the plasma or serum 43 is squeezed out to the plasma or serum sampling aperture 18 and sampled within the collecting cavity 22.

Furthermore, as shown in FIG. 11, another method can be adopted in which in the state that the holding member is pressed with a roller type device, by moving the roller 34 in the direction shown by an arrow, the plasma or serum 43 is squeezed out to the plasma or serum sampling aperture 18 and sampled within the collecting cavity 22. The squeezing operation may be performed with the help of a mechanical separator device as disclosed in EP 2 018 555 A1.

How to squeeze out the plasma or serum is not specifically limited. To be more concrete, for example, it is only required that in the state that the bottom surface of the holding member 14 is firmly kept, for example, located on a flat surface and the upper surface thereof is pressed with a fingernail or a hard tool 48, by moving the fingernail or the hard tool 48 in the direction of the distal end portion shown by an arrow, the plasma or serum 43 is squeezed out to the plasma or serum sampling aperture 18 and sampled within the collecting cavity 22.

Plasma or serum sampled by the above methods can be used for any blood test without any specific limitation. For example, in a case where the plasma or serum sample is used for a measuring examination of a bilirubin concentration, it is preferable to sample the plasma or serum with a capillary tube and to measure it by a bilirubin analyser for exclusive capillary tube use (FIG. 1). Plasma or serum sampled using a plasma or serum separator of the present invention does not differ from plasma or serum sampled using a common centrifuge, and then can be used for every blood test using plasma or serum including a biochemical examination.

With a plasma or serum separator and a plasma or serum sampling method of the present invention, high purity plasma or serum can be easily obtained from a small amount of blood without the use of a centrifuge. With a plasma or serum separator and a plasma or serum sampling method of the present invention, plasma or serum of a liquid state which is not desiccated can be obtained; therefore, the plasma or serum can be directly subjected to a quantitative analysis.

As described above, with a plasma or serum separator of the present invention, an arbitrarily predetermined amount of plasma or serum can be isolated and collected in a liquid or dry state from a very small, indefinite amount of a whole blood sample easily and quickly without leakage and hemolysis of a blood cell component without using a centrifuge or a special device and a tool for pressuring or reducing a pressure. The isolated plasma or serum can be analyzed without transferring the plasma or serum from the separator to further analysis device.

Since plasma or serum can be isolated and collected from a very small amount of whole blood, it is only required to sample blood by sticking a needle into a finger tip or the like of a person to be examined without using a syringe in obtaining a blood test sample; therefore it is possible to reduce a burden imposed on a person to be examined and also to sample blood personally by a person to be examined. Furthermore, using the sampling method of the present invention, a blood test can be performed instantly at any time; it is useful in an emergency test and home-use test. Especially according to the plasma or serum sampling method of the present invention, in measurement on a bilirubin concentration in blood, which is a kernicterus examination for a neonate, blood obtained by sticking a needle in a sole of a neonate is used for sampling plasma or serum into a capillary tube using one of the first to third aspect of the plasma or serum separator of the present invention to instantly enable a bilirubin concentration to be measured using a bilirubin analyzer for exclusive capillary tube use; the method is capable of coping with measurement in hospital, a visiting examination in home after leaving hospital and home-use test at any time.

As no transfer of the blood from the separator to a further analysis device is necessary the method can be executed easily even by the ordinary person or patient without professional medical education or laboratory training. This increases the reliability of the analysis, as possible errors, which may occur during the transfer of blood are avoided. Using the separator and the method of the invention blood tests can be carried out by the patient at home and the time, effort and costs for going to a hospital or medical laboratory can be saved.

Using the plasma or serum separator 10 of the present invention, a great effect is achieved that when isolating plasma or serum from whole blood, not only is isolation of red blood cells quickly effected, but also isolation ability is high, and less of hemolysis is realized. According to the plasma or serum separation method of the present invention, plasma or serum can be quickly isolated from whole blood under suppression of hemolysis without using a centrifuge. According to the test carrier of the present invention, even in a point of care examination in a clinical laboratory test, plasma or serum can be isolated from whole blood substantially without causing hemolysis. According to glass fibers of the present invention, a cell component of non-diluted whole blood can be very well separated from plasma or serum while suppressing hemolysis.

What is claimed is:

1. A plasma or serum separator (10) for isolating plasma or serum from whole blood, the plasma or serum separator (10) being formed as a strip and comprising:
   a blood separation member (12), configured for separating blood applied to a first portion of the blood separation member (12) such that the plasma or serum of the blood is located in a second portion of the blood separation member (12);
   a holding member (14) covering and holding the blood separation member (12), wherein the holding member (14) includes a base film (14a) on its lower side and a covering film (14b) on its upper side with the blood separation member (12) being sandwiched between the base film (14a) and the covering film (14b);
   a blood introducing portion (16) formed in a portion of the holding member (14) covering the first portion of the blood separation member (12);
   a plasma or serum sampling aperture (18) formed in a portion of the holding member (14) covering the second portion of the blood separation member (12),
   characterized in that the separator (10) is configured for plasma or serum to be extracted from the blood separation member (12) through the plasma or serum sampling aperture (18) by applying pressure to the blood separation member (12) in order to squeeze out the plasma or serum and further comprises
   at least one plasma or serum collecting cavity (22) formed within the strip, the at least one plasma or serum collecting cavity (22) being defined by the base film (14a) at its bottom and the covering film (14b) at its sides and arranged at the second portion of the blood separation member (12) in fluid communication with the plasma or serum sampling aperture (18) for collecting plasma or serum leaving the blood separation member (12) through the plasma or serum sampling aperture (18).

2. The plasma or serum separator (10) of claim 1 wherein the plasma or serum collecting cavity (22) is fixed to and/or covered by the holding member (14).

3. The plasma or serum separator (10) of claim 1 wherein the plasma or serum collecting cavity (22) is confined at least partially by a transparent material (24a, 24b) allowing electromagnetic radiation to pass through the collecting cavity (22) and though the plasma or serum collected in the collecting cavity wherein the transparent material (24a, 24b) is in particular transparent for electromagnetic radiation in the range of 380 nm to 780 nm and even more particular for electromagnetic radiation in the range 450 nm to 460 nm.

4. The plasma or serum separator (10) of claim 1 wherein the plasma or serum collecting cavity (22) is at least partially open.

5. The plasma or serum separator (10) of claim 1 wherein the plasma or serum collecting cavity (22) is provided with at least one electrode (26), which is configured to contact the plasma or serum collected in the collecting cavity (22).

6. The plasma or serum separator (10) of claim 5 further comprising an electronic circuit (28) electrically connected to the at least one electrode (26), the electronic circuit (28) being configured to analyse the plasma or serum collected in the collecting cavity (22).

7. The plasma or serum separator (10) of claim 1 comprising a plurality of said plasma or serum collecting cavities (22) fluidly connected individually and in parallel to the plasma or serum sampling aperture (18).

8. The plasma or serum separator (10) of claim 7, wherein at least some of the collecting cavities (22) are connected individually and in parallel to the plasma or serum sampling aperture (18).

9. The plasma or serum separator (10) of claim 7 wherein at least some of the collecting cavities (22) are connected serially to each other.

10. The plasma or serum separator (10) of claim 1, wherein the plasma or serum collecting cavity (22) has a circular, elliptical, angular, in particular triangular, rectangular, hexagonal, octagonal, polygonal shape or any combination thereof.

11. The plasma or serum separator (10) of claim 1 comprising a reagent (32) in at least one of the plasma or serum collecting cavities (22).

12. A plasma or serum sampling method employing a plasma or serum separator (10) according to claim 1, the method comprising the steps of:
   applying blood to the blood introducing portion (16) of the plasma or serum separator (10) to introduce whole blood into the blood separation member (12);
   subjecting the introduced whole blood to separation by the blood separation member (12) such that the plasma or serum is located in the second portion of the blood separation member (12);
   transferring the plasma or serum from the second portion of the blood separation member (12) through the plasma or serum sampling aperture (18) into the plasma or serum collecting cavity (22) by squeezing the plasma or serum out of the blood separation member (12).

13. The plasma or serum sampling method of claim 12 further comprising the step adding a reagent (32) to the plasma or serum in said plasma or serum collecting cavity (22).

14. A method for analyzing plasma or serum comprising the steps of
   sampling plasma or serum with the method of claim 12;
   passing electromagnetic radiation though the plasma or serum collecting cavity (22) and the plasma or serum collected in said collecting cavity (22) and
   measuring the absorption caused by the plasma or serum in said collecting cavity (22).

15. A method for analyzing plasma or serum comprising the steps of sampling plasma or serum with the method of claim 12;
   contacting the plasma or serum collected in the plasma or serum collecting cavity (22) with at least two electrodes (26); and
   measuring the conductance of the plasma or serum collected in said plasma or serum collecting cavity (22).

* * * * *